United States Patent
Hernandez et al.

(10) Patent No.: US 8,821,543 B2
(45) Date of Patent: Sep. 2, 2014

(54) ADJUSTABLE ANCHOR SYSTEMS AND METHODS

(75) Inventors: Joseph Hernandez, Sandwich, MA (US); Mehmet Ziya Sengun, Canton, MA (US); Gerome Miller, Randolph, MA (US)

(73) Assignee: DePuy Mitek, LLC, Raynham, MA (US)

( * ) Notice: Subject to any disclaimer, the term of this patent is extended or adjusted under 35 U.S.C. 154(b) by 0 days.

(21) Appl. No.: 12/977,146

(22) Filed: Dec. 23, 2010

(65) Prior Publication Data

US 2012/0165864 A1 Jun. 28, 2012

(51) Int. Cl.
*A61B 17/04* (2006.01)

(52) U.S. Cl.
USPC ........... 606/232; 606/139; 606/144; 606/145; 606/148; 606/230

(58) Field of Classification Search
USPC ......... 606/139, 144, 145, 148, 223, 224, 225, 606/228, 230, 232; 289/1.5, 17
See application file for complete search history.

(56) References Cited

U.S. PATENT DOCUMENTS

| | | | |
|---|---|---|---|
| 2,566,625 A | 9/1951 | Nagelmann |
| 2,600,395 A | 6/1952 | Domoj et al. |
| 2,697,624 A | 12/1954 | Thomas et al. |
| 2,758,858 A | 8/1956 | Smith |
| 2,992,029 A | 7/1961 | Russell |
| 3,106,417 A | 10/1963 | Clow |
| 3,131,957 A | 5/1964 | Musto |
| 3,177,021 A | 4/1965 | Benham |
| 3,402,957 A | 9/1968 | Peterson |
| 3,521,918 A | 7/1970 | Hammond |
| 3,565,077 A | 2/1971 | Glick |
| 3,580,256 A | 5/1971 | Wilkinson et al. |
| 3,712,651 A | 1/1973 | Shockley |
| 3,752,516 A | 8/1973 | Mumma |

(Continued)

FOREIGN PATENT DOCUMENTS

| | | |
|---|---|---|
| AU | 2008229746 A1 | 10/2008 |
| CA | 2772500 A1 | 9/2013 |

(Continued)

OTHER PUBLICATIONS

Extended European Search Report for Application No. 11190159.1 issued Jul. 6, 2012. (11 pages).

(Continued)

*Primary Examiner* — Vy Q Bui

(57) ABSTRACT

An adjustable anchor system for securing tissue to bone, including an anchor having at least one passage extending from a proximal end toward a distal end. The passage defines a restriction such as a restricted opening. The anchor has at least one bone-engaging feature disposed between the proximal and distal ends. The system further includes a first material formed as a closed loop and capable of being placed through a portion of the tissue, and a second filament having a terminal end, a post limb and a sliding knot tied between the terminal end and the post limb to establish an elongated, adjustable-length loop which extends beyond the proximal end of the anchor and captures the closed loop of the first material. The knot of the second filament is restrained by the restricted opening when tension is applied as desired to the post limb to shorten the elongated loop to draw the tissue toward the anchor.

20 Claims, 8 Drawing Sheets

(56) References Cited

U.S. PATENT DOCUMENTS

| | | |
|---|---|---|
| 3,873,140 A | 3/1975 | Bloch |
| 4,029,346 A | 6/1977 | Browning |
| 4,036,101 A | 7/1977 | Burnett |
| 4,038,988 A | 8/1977 | Perisse |
| 4,105,034 A | 8/1978 | Shalaby et al. |
| 4,130,639 A | 12/1978 | Shalaby et al. |
| 4,140,678 A | 2/1979 | Shalaby et al. |
| 4,141,087 A | 2/1979 | Shalaby et al. |
| 4,186,921 A | 2/1980 | Fox |
| 4,205,399 A | 6/1980 | Shalaby et al. |
| 4,208,511 A | 6/1980 | Shalaby et al. |
| 4,319,428 A | 3/1982 | Fox |
| 4,403,797 A | 9/1983 | Ragland, Jr. |
| 4,510,934 A | 4/1985 | Batra |
| 4,572,554 A | 2/1986 | Janssen et al. |
| 4,792,336 A | 12/1988 | Hlavacek et al. |
| 4,870,957 A | 10/1989 | Goble et al. |
| 4,946,377 A | 8/1990 | Kovach |
| 4,962,929 A | 10/1990 | Melton, Jr. |
| 4,987,665 A | 1/1991 | Dumican et al. |
| 5,062,344 A | 11/1991 | Gerker |
| 5,098,137 A | 3/1992 | Wardall |
| 5,144,961 A | 9/1992 | Chen et al. |
| 5,156,616 A | 10/1992 | Meadows et al. |
| 5,178,629 A | 1/1993 | Kammerer |
| 5,217,495 A | 6/1993 | Kaplan et al. |
| 5,250,053 A | 10/1993 | Snyder |
| 5,250,054 A | 10/1993 | Li |
| 5,259,846 A | 11/1993 | Granger et al. |
| 5,263,984 A | 11/1993 | Li et al. |
| 5,279,311 A | 1/1994 | Snyder |
| 5,282,809 A | 2/1994 | Kammerer et al. |
| 5,284,485 A | 2/1994 | Kammerer et al. |
| 5,312,423 A | 5/1994 | Rosenbluth et al. |
| 5,318,575 A | 6/1994 | Chesterfield et al. |
| 5,376,118 A | 12/1994 | Kaplan et al. |
| 5,391,176 A | 2/1995 | de la Torre |
| 5,395,382 A | 3/1995 | DiGiovanni et al. |
| 5,405,352 A | 4/1995 | Weston |
| 5,450,860 A | 9/1995 | O'Connor |
| 5,454,820 A | 10/1995 | Kammerer et al. |
| 5,456,722 A | 10/1995 | McLeod et al. |
| 5,464,427 A | 11/1995 | Curtis et al. |
| 5,464,929 A | 11/1995 | Bezwada et al. |
| 5,472,446 A | 12/1995 | de la Torre |
| 5,527,323 A | 6/1996 | Jervis et al. |
| 5,534,011 A | 7/1996 | Greene, Jr. et al. |
| 5,540,703 A | 7/1996 | Barker, Jr. et al. |
| 5,549,618 A | 8/1996 | Fleenor et al. |
| 5,562,684 A | 10/1996 | Kammerer |
| 5,569,306 A | 10/1996 | Thal |
| 5,571,139 A | 11/1996 | Jenkins, Jr. |
| 5,573,286 A | 11/1996 | Rogozinski |
| 5,591,207 A | 1/1997 | Coleman |
| 5,593,189 A | 1/1997 | Little |
| 5,595,751 A | 1/1997 | Bezwada et al. |
| 5,597,579 A | 1/1997 | Bezwada et al. |
| 5,607,687 A | 3/1997 | Bezwada et al. |
| 5,618,552 A | 4/1997 | Bezwada et al. |
| 5,620,698 A | 4/1997 | Bezwada et al. |
| 5,628,756 A | 5/1997 | Barker |
| 5,645,850 A | 7/1997 | Bezwada et al. |
| 5,647,616 A | 7/1997 | Hamilton |
| 5,648,088 A | 7/1997 | Bezwada et al. |
| 5,667,528 A | 9/1997 | Colligan |
| 5,683,417 A | 11/1997 | Cooper |
| 5,683,419 A | 11/1997 | Thal |
| 5,685,037 A | 11/1997 | Fitzner et al. |
| 5,698,213 A | 12/1997 | Jamiolkowski et al. |
| 5,700,583 A | 12/1997 | Jamiolkowski et al. |
| 5,702,397 A | 12/1997 | Goble et al. |
| 5,709,708 A | 1/1998 | Thal |
| 5,716,368 A | 2/1998 | de la Torre et al. |
| 5,725,556 A | 3/1998 | Moser et al. |
| 5,728,109 A | 3/1998 | Schulze et al. |
| 5,741,332 A | 4/1998 | Schmitt |
| 5,749,898 A | 5/1998 | Schulze et al. |
| 5,782,864 A | 7/1998 | Lizardi |
| 5,814,069 A | 9/1998 | Schulze et al. |
| 5,859,150 A | 1/1999 | Jamiolkowski et al. |
| 5,899,920 A | 5/1999 | DeSatnick et al. |
| 5,941,900 A | 8/1999 | Bonutti |
| 5,971,447 A | 10/1999 | Steck, III |
| 6,024,758 A | 2/2000 | Thal |
| 6,045,574 A | 4/2000 | Thal |
| 6,143,017 A | 11/2000 | Thal |
| 6,221,084 B1 | 4/2001 | Fleenor |
| 6,267,766 B1 | 7/2001 | Burkhart |
| 6,296,659 B1 | 10/2001 | Foerster |
| 6,319,271 B1 | 11/2001 | Schwartz |
| 6,322,112 B1 | 11/2001 | Duncan |
| 6,517,578 B2 | 2/2003 | Hein |
| 6,527,794 B1 | 3/2003 | McDevitt et al. |
| 6,527,795 B1 | 3/2003 | Lizardi |
| 6,540,750 B2 | 4/2003 | Burkhart |
| 6,547,807 B2 | 4/2003 | Chan et al. |
| 6,641,596 B1 * | 11/2003 | Lizardi ..................... 606/232 |
| 6,641,597 B2 | 11/2003 | Burkhart et al. |
| 6,652,563 B2 | 11/2003 | Dreyfuss |
| 6,660,023 B2 | 12/2003 | McDevitt et al. |
| 6,689,154 B2 | 2/2004 | Bartlett |
| 6,767,037 B2 | 7/2004 | Wenstrom, Jr. |
| 6,887,259 B2 | 5/2005 | Lizardi |
| 6,923,824 B2 | 8/2005 | Morgan et al. |
| 7,029,490 B2 | 4/2006 | Grafton et al. |
| 7,048,754 B2 | 5/2006 | Martin et al. |
| 7,081,126 B2 | 7/2006 | McDevitt et al. |
| 7,217,279 B2 | 5/2007 | Reese |
| 7,226,469 B2 | 6/2007 | Benavitz et al. |
| 7,235,090 B2 | 6/2007 | Buckman et al. |
| 7,285,124 B2 | 10/2007 | Foerster |
| 7,309,337 B2 | 12/2007 | Colleran et al. |
| 7,338,502 B2 | 3/2008 | Rosenblatt |
| 7,381,213 B2 | 6/2008 | Lizardi |
| 7,390,332 B2 | 6/2008 | Selvitelli et al. |
| 7,455,684 B2 | 11/2008 | Gradel et al. |
| 7,582,105 B2 | 9/2009 | Kolster |
| 7,601,165 B2 | 10/2009 | Stone |
| 7,651,509 B2 | 1/2010 | Bojarski et al. |
| 7,654,321 B2 | 2/2010 | Zazovsky et al. |
| 7,658,750 B2 | 2/2010 | Li |
| 7,658,751 B2 | 2/2010 | Stone et al. |
| 7,682,374 B2 | 3/2010 | Foerster et al. |
| 7,695,495 B2 | 4/2010 | Dreyfuss |
| 7,703,372 B1 | 4/2010 | Shakespeare |
| 7,803,173 B2 | 9/2010 | Burkhart et al. |
| 7,875,043 B1 | 1/2011 | Ashby et al. |
| 7,883,528 B2 | 2/2011 | Grafton et al. |
| 7,883,529 B2 | 2/2011 | Sinnott et al. |
| 7,905,903 B2 | 3/2011 | Stone et al. |
| 7,981,140 B2 | 7/2011 | Burkhart |
| 8,012,171 B2 | 9/2011 | Schmieding |
| 8,088,146 B2 | 1/2012 | Wert et al. |
| 8,118,836 B2 | 2/2012 | Denham et al. |
| 8,137,382 B2 | 3/2012 | Denham et al. |
| 8,231,653 B2 | 7/2012 | Dreyfuss |
| 8,231,654 B2 | 7/2012 | Kaiser et al. |
| 8,419,769 B2 | 4/2013 | Thal |
| 2002/0019649 A1 | 2/2002 | Sikora et al. |
| 2002/0029066 A1 | 3/2002 | Foerster |
| 2003/0004545 A1 | 1/2003 | Burkhart et al. |
| 2003/0050667 A1 | 3/2003 | Grafton et al. |
| 2003/0120309 A1 | 6/2003 | Colleran et al. |
| 2003/0130695 A1 | 7/2003 | McDevitt et al. |
| 2003/0229362 A1 | 12/2003 | Chan et al. |
| 2004/0093031 A1 | 5/2004 | Burkhart et al. |
| 2004/0098050 A1 | 5/2004 | Foerster et al. |
| 2004/0153074 A1 | 8/2004 | Bojarski et al. |
| 2004/0172062 A1 | 9/2004 | Burkhart |
| 2004/0236373 A1 | 11/2004 | Anspach |
| 2005/0033363 A1 | 2/2005 | Bojarski et al. |
| 2005/0119696 A1 | 6/2005 | Walters et al. |
| 2005/0251208 A1 | 11/2005 | Elmer et al. |
| 2006/0106423 A1 | 5/2006 | Weisel et al. |

(56) References Cited

U.S. PATENT DOCUMENTS

| | | |
|---|---|---|
| 2006/0178680 A1 | 8/2006 | Nelson et al. |
| 2006/0178702 A1 | 8/2006 | Pierce et al. |
| 2006/0293710 A1 | 12/2006 | Foerster et al. |
| 2007/0027476 A1 | 2/2007 | Harris et al. |
| 2007/0032792 A1 | 2/2007 | Collin et al. |
| 2007/0060922 A1 | 3/2007 | Dreyfuss |
| 2007/0135843 A1 | 6/2007 | Burkhart |
| 2007/0150003 A1 | 6/2007 | Dreyfuss et al. |
| 2007/0156148 A1 | 7/2007 | Fanton et al. |
| 2007/0156149 A1 | 7/2007 | Fanton et al. |
| 2007/0156150 A1 | 7/2007 | Fanton et al. |
| 2007/0156176 A1 | 7/2007 | Fanton et al. |
| 2007/0219557 A1 | 9/2007 | Bourque et al. |
| 2007/0219558 A1 | 9/2007 | Deutsch |
| 2007/0225719 A1 | 9/2007 | Stone et al. |
| 2008/0009901 A1 | 1/2008 | Redmond et al. |
| 2008/0009904 A1 | 1/2008 | Bourque et al. |
| 2008/0065114 A1 | 3/2008 | Stone et al. |
| 2008/0077182 A1 | 3/2008 | Geissler et al. |
| 2008/0091237 A1 | 4/2008 | Schwartz et al. |
| 2008/0103528 A1 | 5/2008 | Zirps et al. |
| 2008/0140092 A1 | 6/2008 | Stone et al. |
| 2008/0147063 A1 | 6/2008 | Cauldwell et al. |
| 2008/0188893 A1 | 8/2008 | Selvitelli et al. |
| 2008/0195205 A1 | 8/2008 | Schwartz |
| 2008/0208265 A1 | 8/2008 | Frazier et al. |
| 2008/0228265 A1 | 9/2008 | Spence et al. |
| 2008/0255613 A1* | 10/2008 | Kaiser et al. .......... 606/232 |
| 2008/0275469 A1 | 11/2008 | Fanton et al. |
| 2009/0036905 A1 | 2/2009 | Schmieding |
| 2009/0062850 A1 | 3/2009 | Ken |
| 2009/0082805 A1 | 3/2009 | Kaiser et al. |
| 2009/0082807 A1 | 3/2009 | Miller et al. |
| 2009/0088798 A1 | 4/2009 | Snyder et al. |
| 2009/0099598 A1 | 4/2009 | McDevitt et al. |
| 2009/0138042 A1 | 5/2009 | Thal |
| 2009/0281568 A1 | 11/2009 | Cendan et al. |
| 2009/0281581 A1 | 11/2009 | Berg |
| 2009/0287246 A1* | 11/2009 | Cauldwell et al. ........ 606/232 |
| 2009/0306711 A1 | 12/2009 | Stone et al. |
| 2009/0312776 A1 | 12/2009 | Kaiser et al. |
| 2009/0312794 A1 | 12/2009 | Nason et al. |
| 2009/0318958 A1 | 12/2009 | Ochiai |
| 2010/0004683 A1 | 1/2010 | Hoof et al. |
| 2010/0016892 A1 | 1/2010 | Kaiser et al. |
| 2010/0094425 A1 | 4/2010 | Bentley et al. |
| 2010/0162882 A1 | 7/2010 | Shakespeare |
| 2010/0204730 A1 | 8/2010 | Maiorino et al. |
| 2010/0249834 A1 | 9/2010 | Dreyfuss |
| 2010/0256677 A1 | 10/2010 | Albertorio et al. |
| 2011/0022083 A1 | 1/2011 | DiMatteo et al. |
| 2011/0077667 A1 | 3/2011 | Singhatat et al. |
| 2011/0190815 A1 | 8/2011 | Saliman |
| 2011/0208240 A1 | 8/2011 | Stone et al. |
| 2011/0238111 A1 | 9/2011 | Frank |
| 2011/0270278 A1 | 11/2011 | Overes et al. |
| 2012/0101523 A1 | 4/2012 | Wert et al. |
| 2012/0130423 A1 | 5/2012 | Sengun et al. |
| 2012/0130424 A1 | 5/2012 | Sengun et al. |
| 2012/0179199 A1 | 7/2012 | Hernandez et al. |
| 2012/0253389 A1 | 10/2012 | Sengun et al. |
| 2012/0253390 A1 | 10/2012 | Sengun |
| 2012/0296375 A1 | 11/2012 | Thal |
| 2013/0261664 A1 | 10/2013 | Spenciner et al. |
| 2013/0296895 A1 | 11/2013 | Sengun |
| 2013/0296896 A1 | 11/2013 | Sengun |
| 2013/0296931 A1 | 11/2013 | Sengun |
| 2013/0296934 A1 | 11/2013 | Sengun |

FOREIGN PATENT DOCUMENTS

| | | |
|---|---|---|
| EP | 0870471 A1 | 10/1998 |
| EP | 1 199 035 A1 | 4/2002 |
| EP | 1 707 127 A1 | 10/2006 |
| EP | 2 277 457 A1 | 1/2011 |
| EP | 2 455 003 A2 | 5/2012 |
| EP | 2 572 650 A1 | 3/2013 |
| WO | 9519139 A1 | 7/1995 |
| WO | 9717901 A1 | 5/1997 |
| WO | 9811825 A1 | 3/1998 |
| WO | 01/06933 A2 | 2/2001 |
| WO | 03/022161 A1 | 3/2003 |
| WO | 2007/109769 A1 | 9/2007 |

OTHER PUBLICATIONS

Extended European Search Report for Application No. 11190157.5 issued Jul. 6, 2012. (10 pages).

EP Search Report for Application No. 11190159.1 issued Feb. 21, 2012. (8 pages).

EP Search Report for Application No. 11190157.5 issued Feb. 27, 2012. (8 pages).

Dahl et al., Biomechanical characteristics of 9 arthroscopic knots. Arthroscopy. Jun. 2010;26(6):813-8.

[No Author Listed] Arthroscopic Knot Tying Manual 2005. DePuy Mitek.

Kemnitzer et al., Handbook of biodegradable Polymers. Eds. Domb et al. Hardwood Acad. Press. 1997;251-72.

Cohn et al., Biodegradable PEO/PLA block copolymers. J Biomed Mater Res. Nov. 1988;22(11):993-1009.

Cohn et al., Polym Preprint. 1989;30(1):498.

Allock, The Encyclopedia of Polymer Science, vol. 13, pp. 31-41, Wiley Intersciences, John Wiley & Sons, 1988.

Vandorpe et al., Handbook of Biodegradable Polymers, edited by Domb, et al., Hardwood Acad. Press, pp. 161-182 (1997).

Heller, Handbook of Biodegradable Polymers, edited by Domb, et al., Hardwood Academic Press, pp. 99-118 (1997).

International Search Report for Application No. PCT/US2011/067119, mailed Jun. 4, 2012. (6 pages).

Extented European Search Report for Application No. 11195100.0 issued Oct. 17, 2012. (7 pages).

[No Author Listed] Gryphon Brochure. DePuy Mitek. 2 pages (undated).

Extended European Search Report for Application No. 13166905.3 issued Aug. 13, 2013 (9 pages).

Extended European Search Report for Application No. 13166907.9, issued Aug. 1, 2013 (6 pages).

Extended European Search Report for Application No. 13166908.7, issued Aug. 23, 2013 (8 pages).

Extended European Search Report for Application No. 13185425.9 issued Dec. 16, 2013 (9 pages).

\* cited by examiner

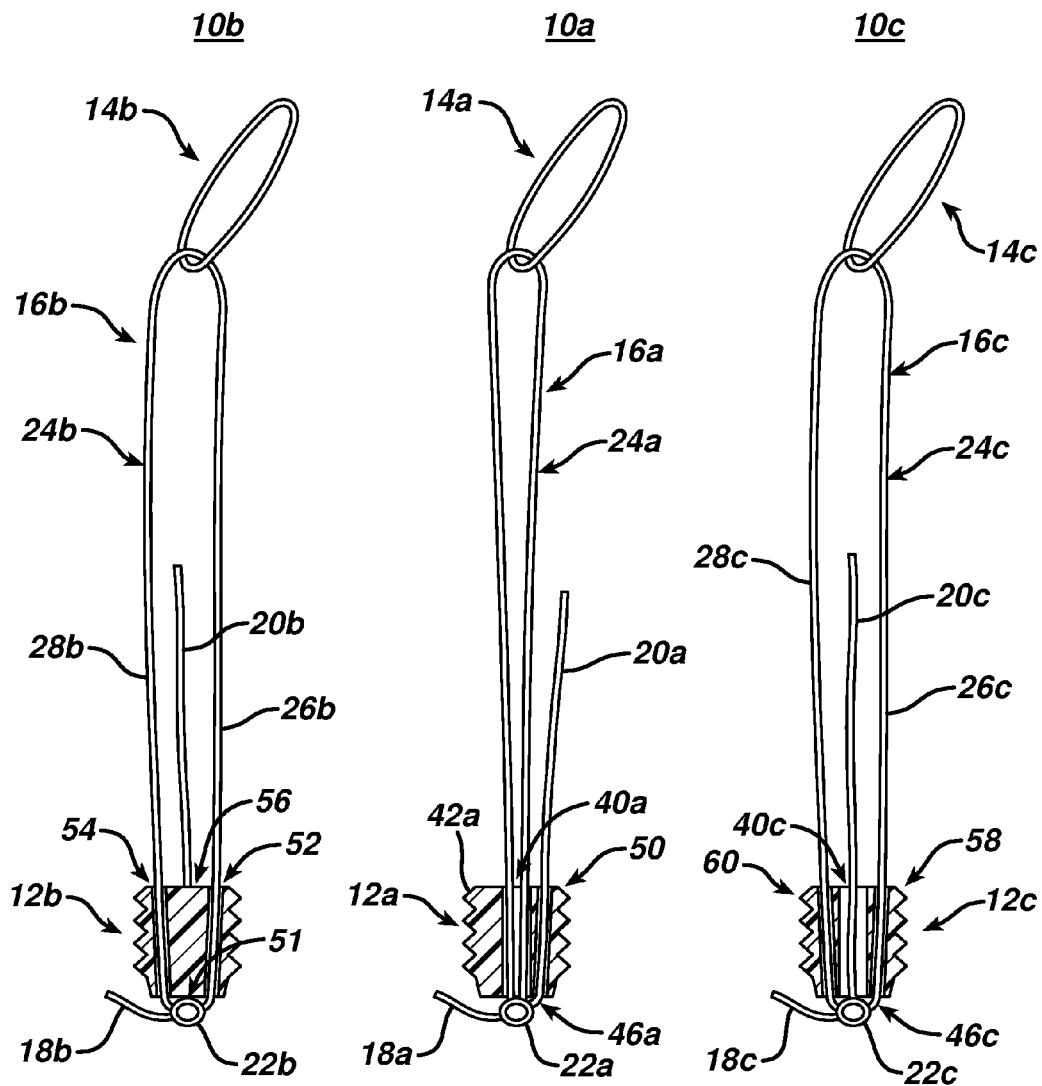

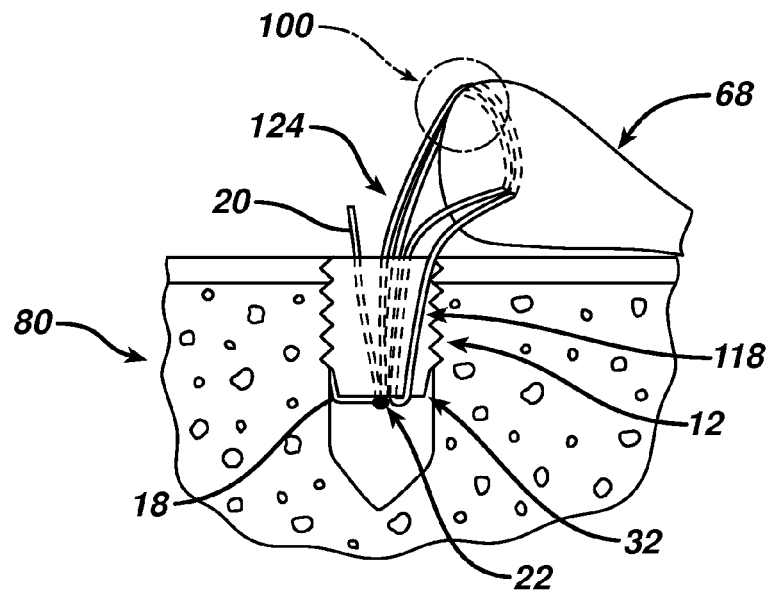
FIG. 8A
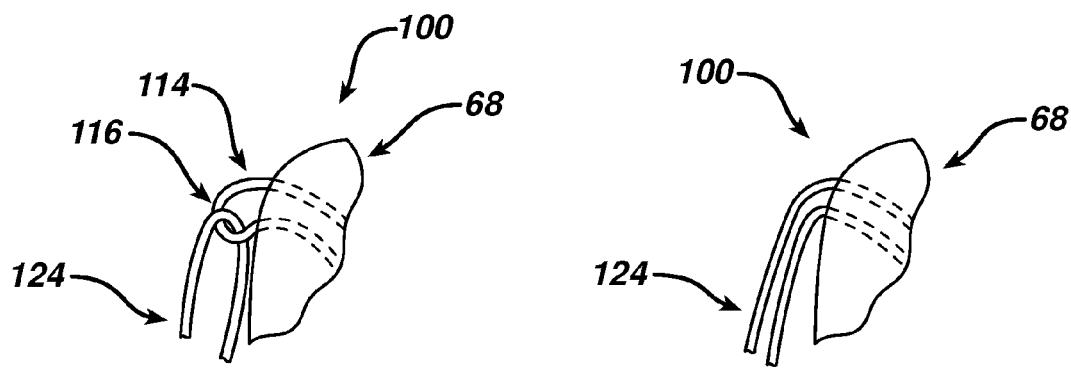
FIG. 8B     FIG. 8C

ADJUSTABLE ANCHOR SYSTEMS AND METHODS

BACKGROUND OF THE INVENTION

1. Field of the Invention

The invention relates to a system and method for securing tissue to bone and more particularly to adjustable tensioning of tissue which eliminates the need for knot-tying by a user.

2. Description of the Related Art

A common injury, especially among athletes, is the complete or partial detachment of tendons, ligaments or other soft tissues from bone. Tissue detachment may occur during a fall, by overexertion, or for a variety of other reasons. Surgical intervention is often needed, particularly when tissue is completely detached from its associated bone. Currently available devices for tissue attachment include screws, staples, suture anchors and tacks. An example of a cannulated suture anchor is provided in U.S. Patent Application Publication No. 2008/0147063 by Cauldwell et al.

There are a number of suture implant systems which proclaim to be "knotless", that is, to not require a surgeon to tie a knot during surgery. Many such systems control tension on tissue by the depth to which an anchor is driven into bone. U.S. Pat. Nos. 5,782,864 and 7,381,213 by Lizardi disclose certain types of suture anchors which capture a fixed-length loop of suture. Adjustable loop knotless anchor assemblies utilizing an anchor element inserted into a sleeve are described by Thal in U.S. Pat. Nos. 5,569,306 and 6,045,574 and in U.S. Patent Application Publication No. 2009/0138042.

Suture anchor systems with sliding knots for repairing torn or damaged tissue, especially for meniscal repair, are disclosed in U.S. Pat. No. 7,390,332 by Selvitelli et al. and are utilized in the OmniSpan™ meniscal repair system commercially available from DePuy Mitek Inc., 325 Paramount Drive, Raynham, Mass. 02767. Other suture anchor systems with sliding and locking knots for repairing tissue include U.S. Pat. No. 6,767,037 by Wenstrom, Jr.

It is therefore desirable to adjust tension on a tissue after an anchor has been fixated in bone without requiring a surgeon to tie any knots, especially during arthroscopic procedures.

SUMMARY OF THE INVENTION

An object of the present invention is to enable tension on tissue to be adjusted independently of anchor fixation and without tying any knots during the procedure.

Another object of the present invention is to enable tissue tension to be adjusted after an anchor driver or other delivery instruments have been removed from the field of view of the tissue and the anchor.

This invention results from the realization that precise tension can be applied to tissue independent of fixation of an anchor in bone by utilizing an elongated, adjustable-length loop of a filament, such as a suture, with a sliding knot, such as a bunt line half hitch knot, having a post limb that can be pulled as desired after the anchor is fixated in bone. As the post limb is pulled, the anchor restrains the knot to hold it in a fixed position and the adjustable loop slides through a closed, preferably fixed-length loop, which passes through the tissue, to draw the tissue toward the anchor until a desired tension is achieved. The anchor continues to restrain the knot while the adjustable loop is under tension and thereby assists in locking the knot.

This invention features an adjustable anchor system for securing tissue to bone, including an anchor having at least one passage extending from a proximal end toward a distal end. The passage defines a restriction such as a restricted opening. The anchor has at least one bone-engaging feature disposed between the proximal and distal ends. The system further includes a first material formed as a closed loop and capable of being placed through a portion of the tissue, and a second filament having a terminal end, a post limb and a sliding knot tied between the terminal end and the post limb to establish an elongated, adjustable-length loop which extends beyond the proximal end of the anchor and captures the closed loop of the first material. The knot of the second filament is restrainable by the restriction when tension is applied to the post limb to shorten the elongated loop to draw the tissue toward the anchor.

In some embodiments, the first material is a first filament. The closed loop of the first filament is substantially shorter in length than the elongated loop of the second filament. In a number of embodiments, the first filament has a diameter at least as large as that of the second filament. In certain embodiments, the first filament is formed to have a lower abrasive property at its surface than that of the second filament. Preferably, the first material is formed from a first suture and the second filament is formed from a second suture. In some embodiments, the first suture has a composition that is different from that of the second suture.

In certain embodiments, the sliding knot is a bunt line half hitch knot. In some embodiments, the passage is defined by at least one inner lumen in the anchor. In another embodiment, the restriction is defined at least in part by engagement with bone when the anchor is fixated in bone, the passage extends along an exterior surface of the anchor traversing the bone-engaging feature, and the bone-engaging feature defines at least one channel as part of the passage.

This invention may also be expressed as an adjustable anchor system for securing tissue to bone, including an anchor having at least one passage extending from a proximal end toward a distal end, the passage defining a restricted opening. The anchor has a circumference and at least one bone-engaging feature disposed between the proximal and distal ends. The system further includes a first filament formed as a closed loop having an opening greater than the circumference of the anchor and capable of being placed through a portion of the tissue, and a second filament having a terminal end, a post limb and a sliding knot tied between the terminal end and the post limb to establish an elongated loop which extends beyond the proximal end of the anchor. The elongated loop captures the first filament and is initially substantially greater in length than the closed loop of the first filament. The knot of the second filament is restrainable by the restricted opening when proximal tension is applied to the post limb after the anchor is fixated in the bone to shorten the elongated loop to draw the tissue toward the anchor.

This invention further features a method for securing tissue to bone, including selecting an anchor having at least one passage extending from a proximal end toward a distal end, the passage defining a restriction, and the anchor having at least one bone-engaging feature disposed between the proximal and distal ends. The method further includes selecting a first filament formed as a closed loop, and selecting a second filament having a terminal end, a post limb and a sliding knot tied between the terminal end and the post limb to establish an elongated loop capturing the closed loop of the first filament at a first location and being initially substantially greater in length than the closed loop. The method also includes placing at least a first portion of the closed loop of the first filament through a portion of the tissue to be secured so that the first portion forms an opening through which the anchor is one of passed and engaged, that is, the anchor is either passed completely through the opening or the first portion is engaged by the anchor. The anchor is then fixated in bone such that the knot of the second filament is restrained by the restriction and the closed loop engages one of the anchor and the elongated loop at a second location. The method further includes applying tension as desired to the post limb after the anchor is fixated in the bone to shorten the elongated loop to draw the tissue toward the anchor.

BRIEF DESCRIPTION OF THE DRAWINGS

In what follows, preferred embodiments of the invention are explained in more detail with reference to the drawings, in which:

FIGS. 1A, 2 and 3 are schematic cross-sectional views of alternative anchor systems according to the present invention;

FIGS. 8A-8C show yet other embodiments in which the closed loop has a sufficient length to extend from the anchor up to and through the tissue, as illustrated in enlarged view in FIG. 8B, and another, less-preferred embodiment in which the closed loop has been eliminated and the adjustable loop passes completely through tissue as illustrated in FIG. 8C.

DETAILED DESCRIPTION OF THE PRESENTLY PREFERRED EMBODIMENTS

This invention may be accomplished by an adjustable anchor system for securing tissue to bone, including an anchor having at least one passage extending from a proximal end toward a distal end. The passage defines a restriction such as a restricted opening or an occluding element. The anchor has at least one bone-engaging feature disposed between the proximal and distal ends. The system further includes a first material, such as a first suture, formed as a closed, preferably fixed-length loop and capable of being placed through a portion of the tissue, and a second filament having a terminal end, a post limb and a sliding knot tied between the terminal end and the post limb to establish an elongated, adjustable-length loop which extends beyond the proximal end of the anchor and captures the closed loop of the first material. The knot of the second filament is restrained by the restricted opening or occluding element when tension is applied as desired to the post limb to shorten the elongated loop to draw the tissue toward the anchor until a desired tension is achieved.

Figure 1:
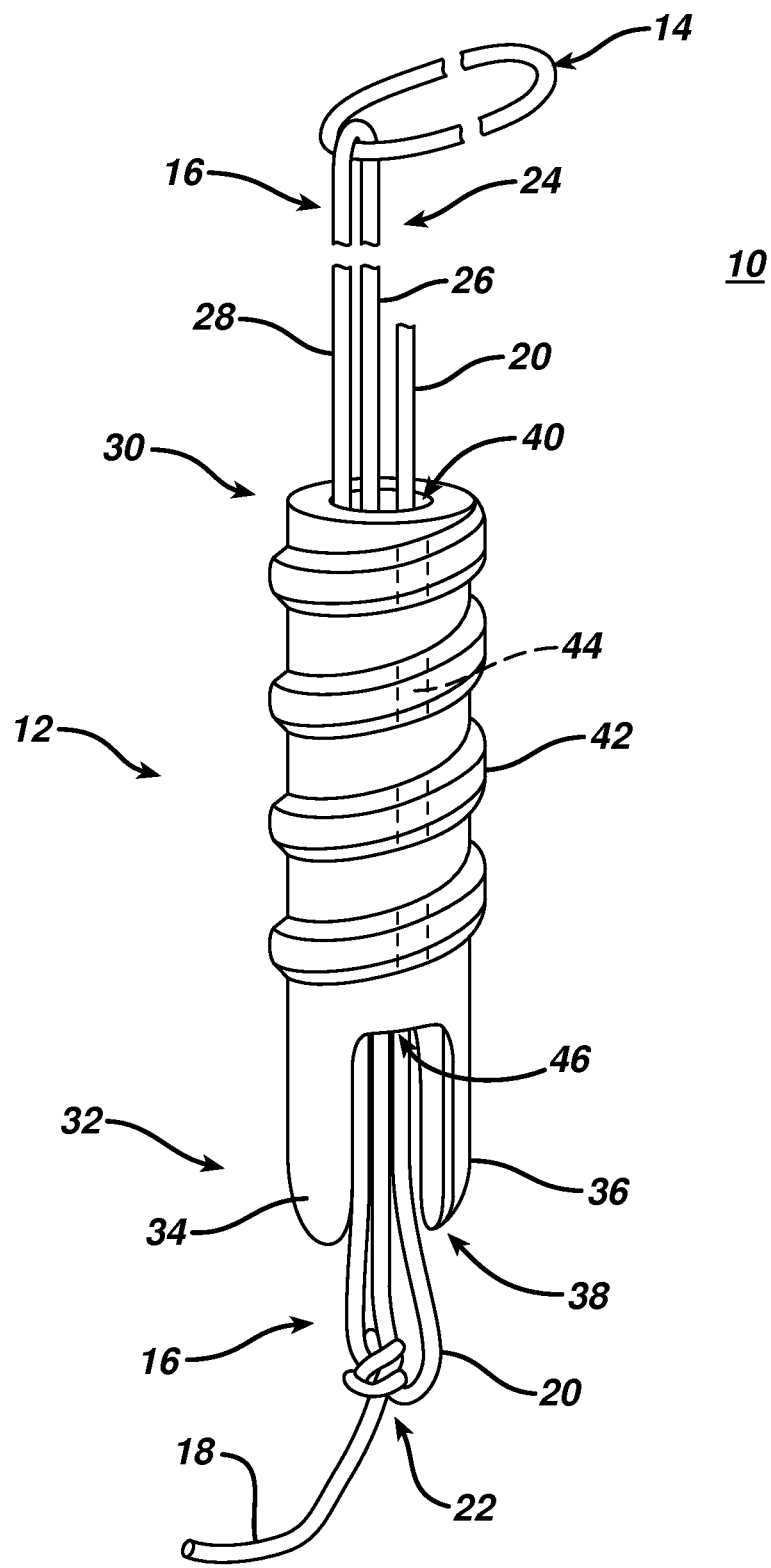
FIG. 1 is a perspective view of an adjustable anchor system according to the present invention having a closed loop and an adjustable loop of filament.

Adjustable anchor system 10, FIG. 1, has a suture anchor 12, a closed, fixed-length loop 14 of a first material, and a second filament 16 having a terminal end 18, a post limb 20, a sliding bunt line half hitch knot 22, and an adjustable loop 24 with loop limbs 26 and 28. In one construction, suture anchor 12 is similar to the cannulated suture anchor disclosed by Cauldwell et al. in U.S. Patent Application Publication No. 2008/0147063, incorporated herein by reference. In anchor systems according to the present invention, however, it is not necessary to have a post-like suture-engaging member or other occluding element over which one or more sutures or suture limbs pass to serve as a restriction to proximal movement; in many constructions, it is sufficient to have a restricted opening 46 to prevent withdrawal of knot 22 as discussed in more detail below, particularly in relation to FIGS. 1A-3.

Suture anchor 12 has a proximal end 30 and a distal end 32 with opposed distal arms 34 and 36 defining cut-out 38 between them. Passage 40 is an inner lumen which runs from proximal end 30 to distal cut-out 38. Although knot 22 is shown extending beyond cut-out 38 in FIG. 1 for purposes of illustration, knot 22 preferably is seated against restricted opening 46 between arms 34 and 36, or otherwise maintained at the distal end 32 by a cavity or other feature, during insertion of anchor system 10 into a patient to minimize interference by the knot 22 with the bone-engaging feature 42, or other exterior surface of anchor 12, and the bone in which suture anchor 12 is fixated.

One or more bone-engaging features 42, such as the helical thread illustrated in FIG. 1 or other features such as teeth, ridges, or other protrusions, are formed on the exterior of anchor 12 to enhance fixation in bone. In one construction, the suture anchor rotates to toggle into bone at its proximal end to minimize withdrawal. In a number of constructions, a hole is formed in bone prior to anchor insertion; in other constructions, a suture anchor is inserted directly into bone.

One or more passages or channels may be formed on the exterior of the suture anchor, such as channel 44 illustrated in phantom, FIG. 1, traversing bone-engaging element 42. Other configurations are illustrated in FIGS. 1A, 2 and 3 for adjustable anchor systems 10a, 10b and 10c, respectively, according to the present invention, having first, fixed-length loops 14a, 14b, 14c and second, adjustable length filaments 16a, 16b, 16c, respectively. Anchor 12a, FIG. 1A, defines an inner lumen 40a and an external passage 50 extending from the distal end to the proximal end of anchor 12a. Sliding knot 22a, formed in second filament 16a, is seated against restricted opening 46a, adjustable loop 24a extends through passage 40a to capture closed loop 14a, and post limb 20a lies within external channel 50 in this construction.

It is a matter of surgeon preference whether a terminal end, such as terminal end 18a, FIG. 1A, is kept at a length sufficient to lie against the exterior of at least one bone-engaging feature 42a to be trapped against bone during insertion, or is trimmed to a shorter length. Different examples of terminal end length are provided in FIGS. 6-8 below. Further, a restriction such as restricted opening 46a may be defined at least in part by engagement with bone when anchor 12a is fixated in bone to prevent knot 22a from moving with post limb 20a when tension is applied to post limb 20a as described in more detail below for procedures of using an anchor system according to the present invention.

Anchor system 10b, FIG. 2, has at least three external passages or channels 52, 54 and 56 without any internal passages in this construction. Knot 22b is maintained at the distal end of anchor 12b by occlusion 51, defined at least in part by the distal surface of anchor 12b, while limbs 26b, 28b of loop 24b lie within passages 52, 54 and post limb 20b of second filament 16b lies within passage 56. As described above, occlusion 51 may be defined in part by engagement of anchor 12b with bone after fixation.

Anchor system 10c, FIG. 3, has an internal passage 40c through which post limb 20c extends from a restricted opening 46c which holds knot 22c. External passages 58, 60 carry limbs 26c, 28c of adjustable loop 16c. Although anchors 12a, 12b and 12c are shown without distal-extending arms in those constructions, in other constructions one or more such distal extensions or other protrusions are provided, similar in some constructions to Cauldwell et al. cited above or to U.S. Pat. No. 7,381,213 by Lizardi, also incorporated herein by reference. In yet other constructions, a cylindrical or otherwise circumferential cavity, bowl or countersink feature is provided at the distal end of the anchor to seat the knot 22 during insertion and fixation.

In preferred constructions, loop 14, also referred to as a first filament, and second filament 16 are formed of one or more types of sutures. Acceptable diameters for second filament 16 include size 0 or size 2 suture, such as Orthocord™ suture commercially available from DePuy Mitek, while the same or larger diameters such as size 2 to size 5 suture are preferred for loop 14, such as Ethibond™ suture available from Ethicon. Orthocord™ suture is approximately fifty-five to sixty-five percent PDS™ polydioxanone, which is bioabsorbable, and the remaining percent ultra high molecular weight polyethylene, while Ethibond™ suture is primarily high strength polyester. In some constructions, especially for shoulder repair procedures, loop 14 has a fixed length of approximately one inch while adjustable loop 24 has a length of at least eighteen inches. The amount and type of bioabsorbable material, if any, utilized in the first or second filament is primarily a matter of surgeon preference for the particular surgical procedure to be performed.

While the same type of suture can be used for both loop 14 and filament 16, a suture having a lower abrasive property at its surface is preferred for the first material forming closed loop 14. The lower abrasive property can be achieved by a larger diameter, a softer composition, a softer braid, plait or strand pattern, or a combination of such characteristics. In some constructions, the suture material for closed loop 14 is tied with a fixed knot to form the fixed-length loop 14. In other constructions, loop 14 is molded or otherwise formed as a ring of material.

Slidable knot 22 has been described as a bunt line half hitch knot in some constructions, but other suitable knots will be readily apparent to those of ordinary skill in the suture tying art after reviewing the present invention. The term "slidable" as used herein is intended to include slidable, lockable knots as well as slidable knots. Several types of suitable knots are described in the Arthroscopic Knot Tying Manual (2005) available from DePuy Mitek, as well as in U.S. Pat. No. 6,767,037 by Wenstrom, Jr.

One procedure according to the present invention for utilizing a cannulated anchor system similar to that shown in FIG. 1 is illustrated in FIGS. 4-7 for attaching tissue 68 to bone 80. Reference numerals utilized to describe the system shown for this procedure follow the numerals utilized for system 10, FIG. 1, for simplicity and clarity, although a number of other types of anchors with different filament limb arrangements as illustrated in other Figures could also be utilized in a similar manner. An initial suture 70, FIG. 4, having a needle 72 at its distal end is passed through tissue 68 to draw at least closed loop 14 at least partially through tissue 68. Alternatively, a suture passing instrument is inserted through tissue 68 to grasp the closed loop 14 and pull it through the tissue 68. The extent to which elongated, adjustable loop 24 is drawn through tissue 68, and whether an anchor passes through or engages the closed loop 14 or adjustable loop 24, are described in more detail below relative to FIGS. 8-8C.

Figure 4:
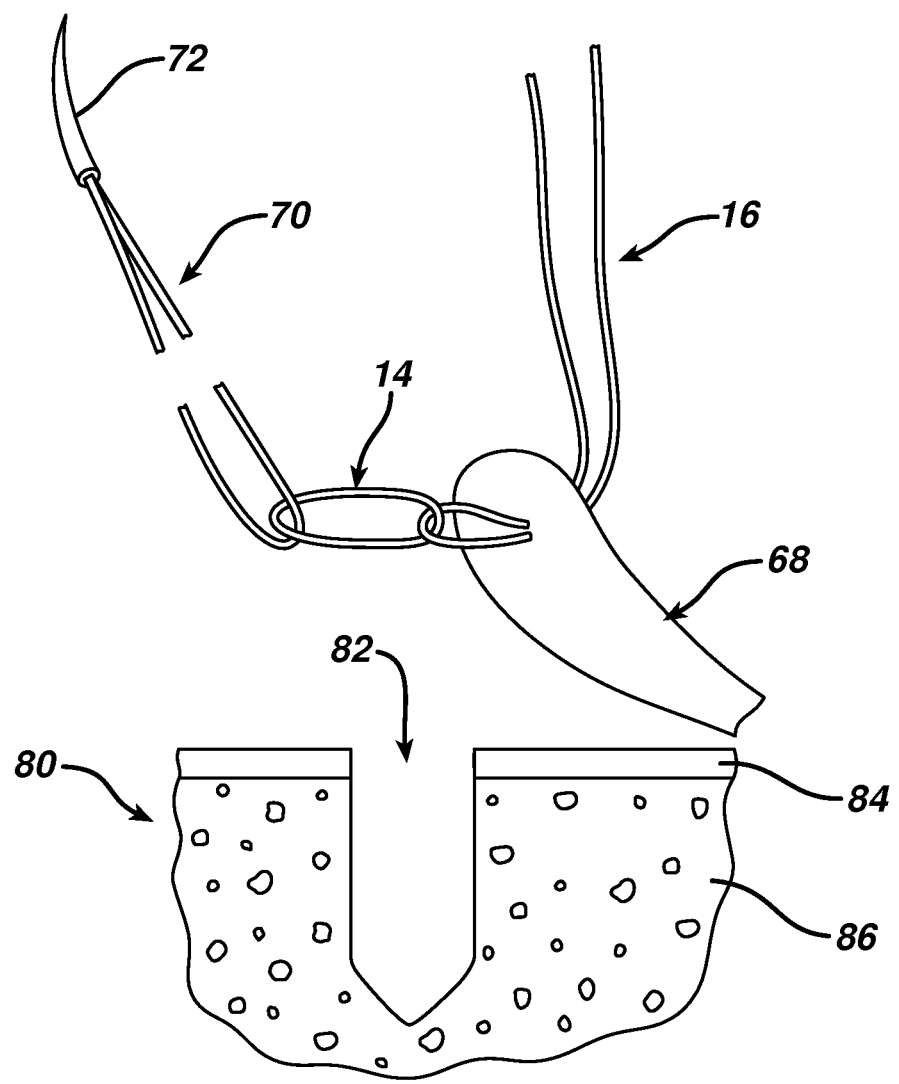
FIG. 4 is a schematic view of a closed loop after it has been pulled through a portion of tissue to be secured to bone, which may draw a portion of the adjustable loop with it through the tissue.
Figure 5:
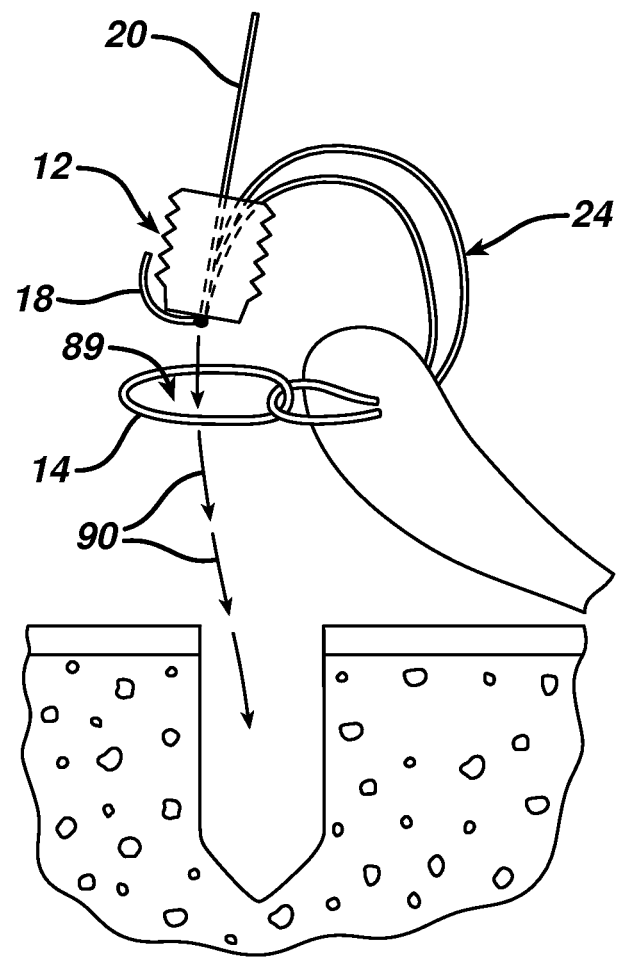
FIG. 5 illustrates an anchor being passed through the fixed loop and directed toward a hole formed in the bone.
Figure 6:
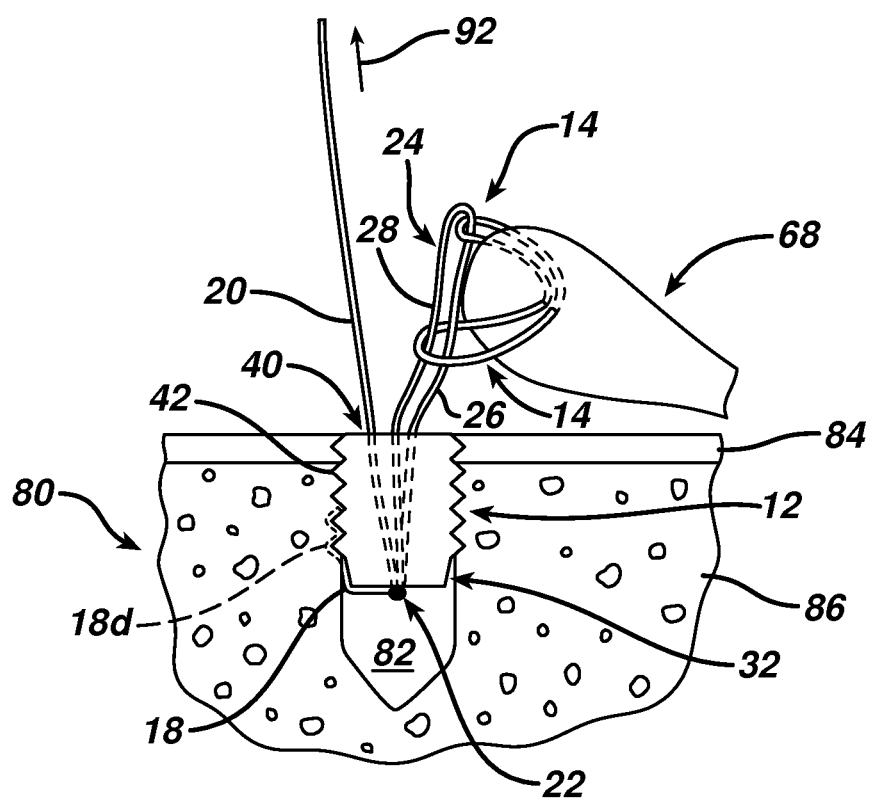
FIG. 6 shows the anchor fixated in bone with tension to be applied on the post limb.

In this procedure, a hole 82, FIG. 4, is formed through compact layer 84 into cancellous layer 86 of bone 80 at a desired repair location. Anchor 12, FIG. 5, is passed through an opening 89 in closed loop 14 as indicated by arrows 90 and is fixated in bone as shown in FIG. 6. Preferably, post limb 20 is extracted from the closed loop 14 after anchor 12 passes through the opening 89 in closed loop 14, FIG. 5, so that post limb 20 can pull directly one of adjustable loop limbs through the knot 22 without being constrained by closed loop 14. Terminal end 18 is trapped between bone 86 and a portion of distal end 32 of anchor 12 in this construction, and sliding knot 22 is held by a restricted opening in internal lumen 40. Alternatively, terminal end 18 has a sufficient length so that it extends proximally along the exterior of the anchor 12 past a plurality of bone engaging features 42 as illustrated in phantom as length 18d, or is a shorter length 18e as shown in FIG. 8.

Figure 7:
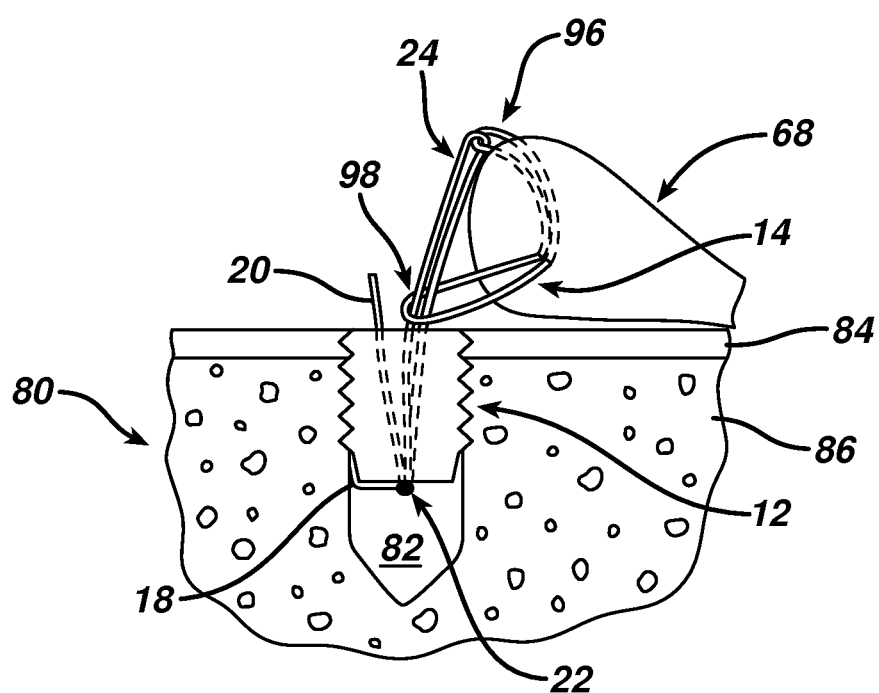
FIG. 7 illustrates the tissue in a desired position under final tension after the post limb has been trimmed.

After fixation of anchor 12, FIG. 6, proximal tension is applied to post limb 20 as indicated by arrow 92. As post limb 20 is moved proximally, adjustable loop 24 readily slides through closed loop 14 as limbs 26 and 28 are shortened. Tissue 68 is thereby drawn toward anchor 12 until a final desired position, under desired tension, is achieved as shown in FIG. 7. Closed loop 14 engages the elongated loop 24 at first and second locations 96 and 98.

Figure 8:
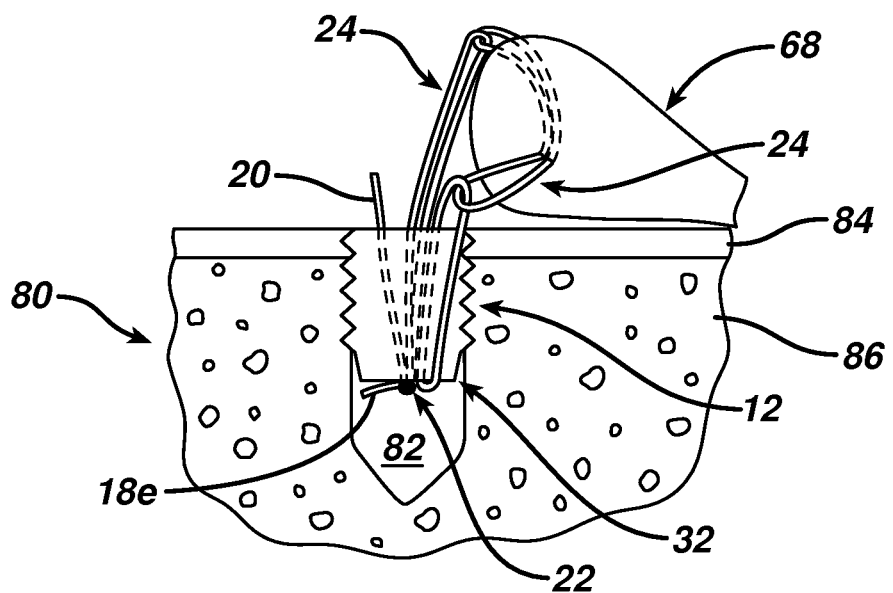
FIG. 8 shows an alternative technique to that illustrated in FIGS. 6 and 7 in which the anchor engages the closed loop instead of passing through it.

Other systems and methods according to the present invention are shown in FIGS. 8-8C as alternatives to the final configuration shown in FIG. 7. Terminal end 18e, FIG. 8, is intentionally short so that it is not trapped between the anchor 12 and bone 80. In this construction, terminal end 18e remains within the bone hole 82 and is not placed under tension of any type.

Instead of requiring an opening 89, FIG. 5, in closed loop 14 to be greater than the circumference of the anchor 12 so that anchor 12 can pass completely through the closed loop 14, in other constructions the distal end 32 engages a portion of the closed loop 14 as shown in FIG. 8. Filament engagement can be accomplished such as shown in FIGS. 11 and 12 of U.S. Pat. No. 7,381,213 by Lizardi. However, one benefit achieved by the present invention is that further tensioning of tissue 68 is possible after anchor fixation by pulling on the post limb of the adjustable loop. Another benefit of the present invention is that the anchor inserter or driver and related driver instruments are removed prior to final tensioning and positioning of the tissue to be repaired to provide improved visual and tactile feedback to the surgeon.

Other arrangements of filaments are illustrated in FIGS. 8A-8C. Anchor 12, FIG. 8A, engages filament portion 118 which passes through tissue 68 to emerge at the other, proximal side in the circled region indicated at 100. In the construction shown in FIG. 8B for that circled region 100, adjustable loop 124 passes through a portion of closed loop 114. In other words, the same filament limbs form portions 114 and 118 of a single closed, fixed-length loop. This arrangement is preferred because the limbs of adjustable loop 124 are able to slide over the closed loop filament at location 116 without passing through tissue as adjustable loop 124 is reduced in size.

In contrast, limbs of adjustable portion 124 pass through tissue 68 in FIG. 8C, which represents an alternative configuration for FIG. 8A, and the adjustable limbs emerge to form portion 118 which is engaged by the distal end 32 of anchor 12. In other words, no closed loop is utilized in the configuration represented by FIG. 8C. However, eliminating the fixed-length loop is less desirable because the adjustable loop may tend to lock on itself, and may bind with or cause damage to the soft tissue through which it passes. The adjustable loop may be prone to locking on itself even if the anchor is passed completely through the adjustable loop. Further, adjustability of portion 118, FIG. 8C, may be further impeded by an interference fit with bone, unless the limbs of portion 118 are properly aligned in channels or other exterior passages along anchor 12.

Thus, while there have been shown, described, and pointed out fundamental novel features of the invention as applied to a preferred embodiment thereof, it will be understood that various omissions, substitutions, and changes in the form and details of the devices illustrated, and in their operation, may be made by those skilled in the art without departing from the spirit and scope of the invention. For example, it is expressly intended that all combinations of those elements and/or steps that perform substantially the same function, in substantially the same way, to achieve the same results be within the scope of the invention. Substitutions of elements from one described embodiment to another are also fully intended and contemplated. It is also to be understood that the drawings are not necessarily drawn to scale, but that they are merely conceptual in nature. It is the intention, therefore, to be limited only as indicated by the scope of the claims appended hereto.

Every issued patent, pending patent application, publication, journal article, book or any other reference cited herein is each incorporated by reference in their entirety.

What is claimed is:

1. An adjustable anchor system for securing tissue to bone, comprising;
    an anchor having at least one passage extending from a proximal end toward a distal end, the passage including a restriction formed distally of the proximal end of the anchor, and the anchor having at least one bone-engaging feature disposed between the proximal and distal ends;
    a first material formed as a closed loop and capable of being placed through a portion of the tissue;
    a second filament having a terminal end, a post limb and a sliding knot tied between the terminal end and the post limb to establish an elongated, adjustable-length loop which extends beyond the proximal end of the anchor and captures the closed loop of the first material; and
    the knot of the second filament being located such that a portion of the anchor is disposed between the knot and the first material, with the knot located at a distal portion of the anchor and the first material located proximal of the proximal end of the anchor, the knot being restrainable by the restriction when tension is applied to the post limb to shorten the elongated loop to draw the tissue toward the anchor.

2. The anchor system of claim 1 wherein the first material is a first filament.

3. The anchor system of claim 2 wherein the closed loop of the first filament is substantially shorter than the elongated loop of the second filament.

4. The anchor system of claim 2 wherein the first filament has a diameter at least as large as that of the second filament.

5. The anchor system of claim 2 wherein the first filament is formed to have a lower abrasive property at its surface than that of the second filament.

6. The anchor system of claim 1 wherein the first material is formed from a first suture and the second filament is formed from a second suture.

7. The anchor system of claim 6 wherein the first suture has a composition that is different from that of the second suture.

8. The anchor system of claim 1 wherein the sliding knot is a bunt line half hitch knot.

9. The anchor system of claim 1 wherein the passage is defined by at least one inner lumen in the anchor.

10. The anchor system of claim 1 wherein the restriction is defined at least in part by engagement with bone when the anchor is fixated in bone.

11. The anchor system of claim 1 wherein the passage extends along an exterior surface of the anchor traversing the bone-engaging feature, and the bone-engaging feature defines at least one channel as part of the passage.

12. The anchor system of claim 1, wherein the at least one passage extends through a whole length of the anchor from the proximal end to the distal end.

13. The anchor system of claim 1, wherein the anchor has a channel extending therethrough, the post limb being disposed through the channel.

14. An adjustable anchor system for securing tissue to bone, comprising;
    an anchor having at least one passage extending from a proximal end toward a distal end, the passage defining a restricted opening, the anchor having a circumference and the anchor having at least one bone-engaging feature disposed between the proximal and distal ends;
    a first filament formed as a closed loop having an opening greater than the circumference of the anchor and capable of being placed through a portion of the tissue;
    a second filament having a terminal end, a post limb and a sliding knot tied between the terminal end and the post limb to establish an elongated, adjustable-length loop which extends beyond the proximal end of the anchor, the elongated loop capturing the first filament and being initially substantially greater in length than the closed loop of the first filament; and
    the knot of the second filament being located such that a portion of the anchor is disposed between the knot and the first filament, with the knot located at a distal portion of the anchor and the first filament located proximal of the proximal end of the anchor, the knot being restrainable by the restricted opening at a position distal to the proximal end of the anchor when proximal tension is applied to the post limb after the anchor is fixated in the bone to shorten the elongated loop to draw the tissue toward the anchor.

15. The anchor system of claim 14 wherein the first filament is formed from a first suture and the second filament is formed from a second suture.

16. The anchor system of claim 15 wherein the first suture has a composition that is different from that of the second suture.

17. The anchor system of claim 15 wherein the sliding knot is a bunt line half hitch knot.

18. The anchor system of claim 14 wherein the passage is defined by at least one inner lumen in the anchor.

19. The anchor system of claim 14, wherein the at least one passage extends through a whole length of the anchor from the proximal end to the distal end.

20. The anchor system of claim 14, wherein the anchor has a channel extending therethrough, the post limb being disposed through the channel.

* * * * *